United States Patent
Kajiki (10) Patent No.: US 8,481,939 B2
(45) Date of Patent: Jul. 9, 2013

(54) PHOTOCONDUCTIVE DEVICE, AND TERAHERTZ WAVE GENERATION AND DETECTION APPARATUSES EACH USING THE PHOTOCONDUCTIVE DEVICE

(75) Inventor: Kousuke Kajiki, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 458 days.

(21) Appl. No.: 12/792,619

(22) Filed: Jun. 2, 2010

(65) Prior Publication Data

US 2010/0310976 A1     Dec. 9, 2010

(30) Foreign Application Priority Data

Jun. 5, 2009   (JP) ................... 2009-135630

(51) Int. Cl.
*G01T 7/00*        (2006.01)
(52) U.S. Cl.
USPC .................................. 250/336.1; 250/504 R
(58) Field of Classification Search
USPC .......................................... 250/336.1, 504 R
See application file for complete search history.

(56) References Cited

U.S. PATENT DOCUMENTS

| | | | | |
|---|---|---|---|---|
| 5,894,125 A * | 4/1999 | Brener et al. | ................. | 250/330 |
| 6,909,104 B1 * | 6/2005 | Koops et al. | ................ | 250/493.1 |
| 2003/0184328 A1 * | 10/2003 | Lee et al. | ..................... | 324/750 |
| 2007/0034813 A1 * | 2/2007 | Shen et al. | ................. | 250/493.1 |

FOREIGN PATENT DOCUMENTS

JP          2006-86227 A        3/2006

* cited by examiner

*Primary Examiner* — Casey Bryant
(74) *Attorney, Agent, or Firm* — Canon U.S.A., Inc. IP Division (57) ABSTRACT

A photoconductive device includes: a photoconductive layer configured to generate carriers upon irradiation with excitation light, a first electrode arranged on the photoconductive layer, a second electrode arranged on the photoconductive layer with a gap between the first and second electrodes, and a third electrode arranged in a region over which an electric field caused by voltages applied to the first and second electrodes or an electric field caused by irradiation with a terahertz wave extends. A depletion layer of the photoconductive layer is controllable by a voltage applied to the third electrode.

8 Claims, 11 Drawing Sheets

PHOTOCONDUCTIVE DEVICE, AND TERAHERTZ WAVE GENERATION AND DETECTION APPARATUSES EACH USING THE PHOTOCONDUCTIVE DEVICE

BACKGROUND OF THE INVENTION

1. Field of the Invention

The present invention relates to a photoconductive device. The present invention also relates to a terahertz wave generation apparatus and a terahertz wave detection apparatus that each use the photoconductive device.

2. Description of the Related Art

Terahertz waves are electromagnetic waves having any components of frequency bands within a range from 0.03 THz to 30 THz. In the terahertz wave band, there exist many characteristic absorptions that depend on the structures and states of various materials including biological molecules. Utilizing such a characteristic, nondestructive inspection technologies for analyzing and identifying materials have been developed. Terahertz waves are also expected to be applied to safe imaging technologies replacing X-ray technology and high-speed communications technologies.

One of the important factors for making these technologies practically usable is the advance in terahertz wave generation and detection technologies. As a terahertz wave generation technology, a photoconductive device technology has been disclosed (see Japanese Patent Laid-Open No. 2006-86227). The photoconductive device described in this document uses a photoconductive layer of indium gallium arsenide (InGaAs) that can efficiently absorb 1.5 μm band excitation light. Further, photoconductive devices with increased resistance have been disclosed, such as a device in which iron (Fe) ions have been injected in the photoconductive layer thereof and a device in which a portion of the photoconductive layer thereof other than a portion irradiated with excitation light has been removed. These devices, in the case of photoconductive devices appropriate for 1.5 μm excitation light, may be able to generate high-intensity terahertz waves.

Hitherto, the thickness of a photoconductive layer has been made larger than an optical absorption length for the excitation light wavelength in order to increase the absorption amount of the excitation light. However, this makes the thickness of the photoconductive layer larger than that of a depletion layer, and thereby sometimes causes a decrease in the resistance of the photoconductive layer. When the resistance of a photoconductive device is low, an applied voltage causes a high current to flow, which is likely to damage the photoconductive device. This causes a voltage applied to a photoconductive device to be lowered. Since terahertz waves are generated when photo-excited carriers are accelerated by an electric field within a photoconductive layer, the intensity of terahertz wave radiation is likely to be small if a voltage which can be applied to the photoconductive device is low as described above. It is hard to claim that such problems have been solved even by the technology disclosed in Japanese Patent Laid-Open No. 2006-86227.

SUMMARY OF THE INVENTION

The present invention provides a photoconductive device that allows the resistance thereof to be controlled by controlling a depletion layer in a photoconductive layer.

As an aspect of the present invention, a photoconductive device includes: a photoconductive layer configured to generate carriers upon irradiation with excitation light, a first electrode arranged on the photoconductive layer, a second electrode arranged on the photoconductive layer with a gap between the first and second electrodes, and a third electrode arranged in a region over which an electric field caused by voltages applied to the first and second electrodes or an electric field caused by irradiation with a terahertz wave extends. A depletion layer of the photoconductive layer is controllable by a voltage applied to the third electrode.

Further aspects of the present invention will become apparent from the following description of exemplary embodiments with reference to the attached drawings.

DESCRIPTION OF THE EMBODIMENTS

Hereinafter, embodiments of the present invention are described. In the present invention, it is important that a third electrode be provided within a region covered by an electric field caused by a voltage applied to first and second electrodes or an electric field caused by irradiation with terahertz waves. On the basis of this concept, the basic embodiments of the photoconductive device according to the present invention have the configuration described above. That is, first, second, and third electrodes are arranged on a photoconductive layer for generating carriers through irradiation with excitation light. There is a gap between the second electrode and the first electrode, and a voltage applied to the third electrode can control the depletion layer of the photoconductive layer. More specifically, a group of electrodes including the first and second electrodes is formed in such a manner as to contact the photoconductive layer directly or indirectly, and includes two or more electrodes (typically a pair of electrodes) having gaps thereamong in a region of the photoconductive layer where photo-excited carriers are generated. At least part of the third electrode is within a region covered by an electric field caused by a voltage applied to the group of electrodes or an electric field caused by irradiation with terahertz waves. As long as the third electrode can control the depletion layer while the above conditions are satisfied and the group of electrodes and the third electrode have different voltages, the third electrode may be arranged in any way with respect to the photoconductive layer. The third electrode may be formed in such a manner as to be in direct or indirect contact with the photoconductive layer, or partly or fully embedded in the photoconductive layer.

An embodiment which can realize the idea of the present invention will now be described with reference to the drawings. Note that for ease of description, some portions are illustrated using different scales, resulting in deformation.

First Embodiment

Figure 1A:
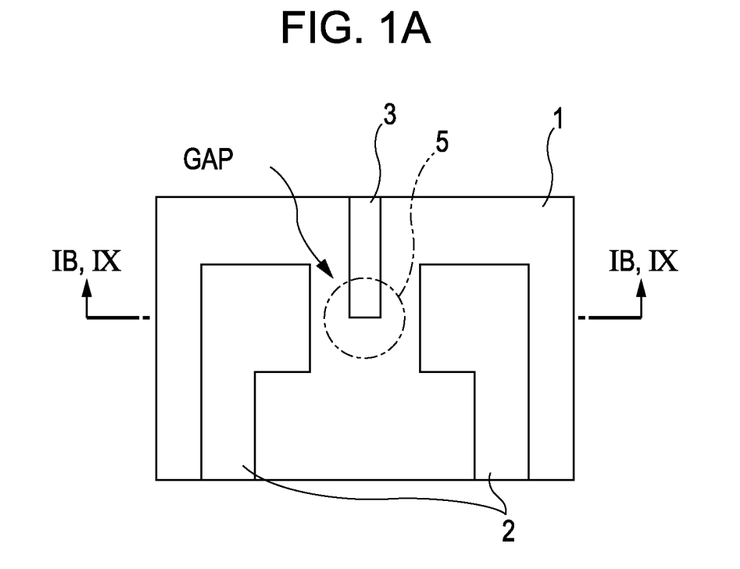
FIG. 1A is a top view of a general configuration of a photoconductive device according to a first embodiment.
Figure 1B:
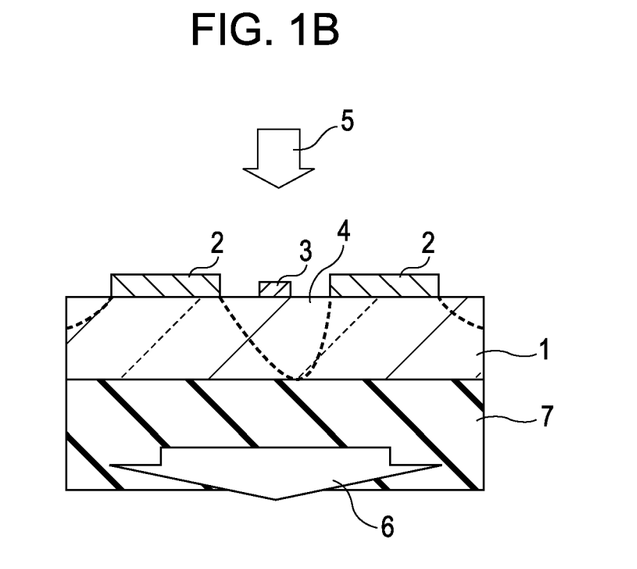
FIG. 1B is a sectional view taken along the line IB-IB of FIG. 1A.
Figure 1C:
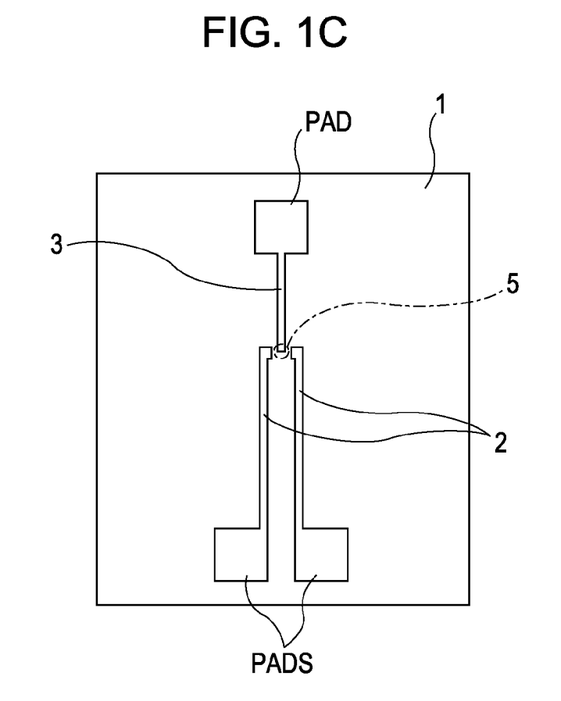
FIG. 1C is a general view of the photoconductive device of the first embodiment.

A photoconductive device according to a first embodiment of the invention is described. FIG. 1A is a top view of a general configuration of a photoconductive device according to the present embodiment, FIG. 1B is a sectional view taken along the line IB-IB of FIG. 1A, and FIG. 1C is a general view of the photoconductive device according to the present embodiment. FIG. 1A illustrates a magnified view of a portion of FIG. 1C where a terahertz wave 6 is generated by irradiation with excitation light 5. Referring to FIGS. 1A to 1C, the photoconductive device according to the present embodiment includes a substrate 7, a photoconductive layer 1, a pair of electrodes 2 constituted by first and second electrodes, and a third electrode 3. In the present embodiment, a group of electrodes is the pair of electrodes constituted by the first and second electrodes formed in such a manner as to be directly or indirectly in contact with the photoconductive layer 1. However, as long as an electric-field-generated region having a certain range is realized on the photoconductive layer 1, any number, shape, and arrangement of the group of electrodes may be used. Similarly, although the third electrode is constituted by one electrode which is formed in such a manner as to be directly or indirectly in contact with the photoconductive layer 1, any number, shape, and arrangement thereof may be used, as long as the thickness and area of a depletion layer 4 can be changed in at least part of the electric-field-generated region.

The materials, arrangement, and the like of the components are described. The substrate 7 preferably is made of a material having high insulation. Examples of materials that can be used for the substrate 7 include semi-insulating gallium arsenide (SI-GaAs) and semi-insulating indium phosphide (SI-InP). A material with low absorption in a terahertz wave region, such as silicon (Si) may also be used. The photoconductive layer 1 is arranged on the substrate 7. The photoconductive layer 1 is made of a material that generates photo-excited carriers upon irradiation with the excitation light 5. Examples of such materials that can be used include gallium arsenide (GaAs) for the excitation light 5 in the 0.8 μm wavelength band, and indium gallium arsenide (InGaAs) for the excitation light 5 in the 1.5 μm wavelength band. The material of the photoconductive layer 1 may be a low-temperature-grown material, which is said to have a characteristic suitable for terahertz wave generation, or a material other than a low-temperature-grown material. The photoconductive layer 1 need not cover the whole upper surface of the substrate 7, and needs only be at least in a region where photo-excited carriers are generated by irradiation with the excitation light 5.

Figure 6A:
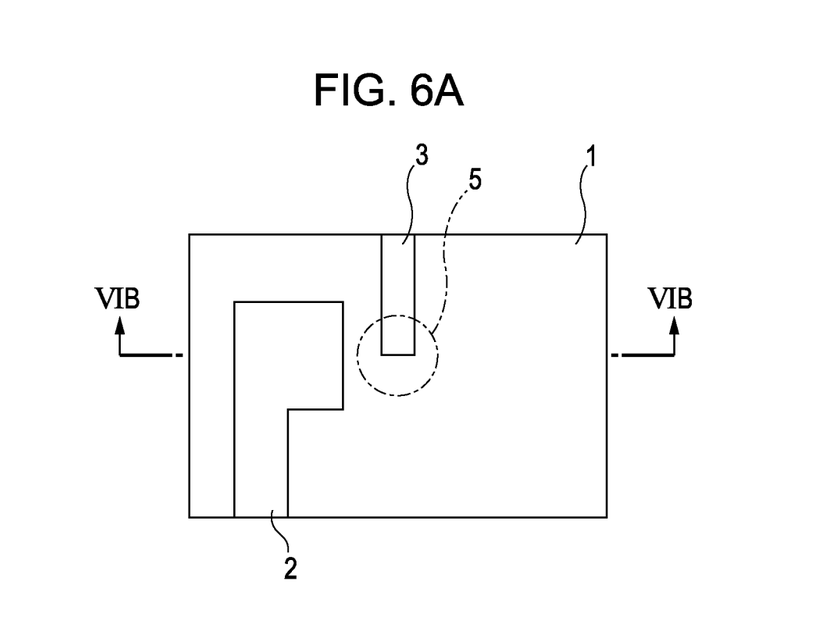
FIG. 6A is a top view of another modification example of the photoconductive device of the first embodiment.
Figure 6B:
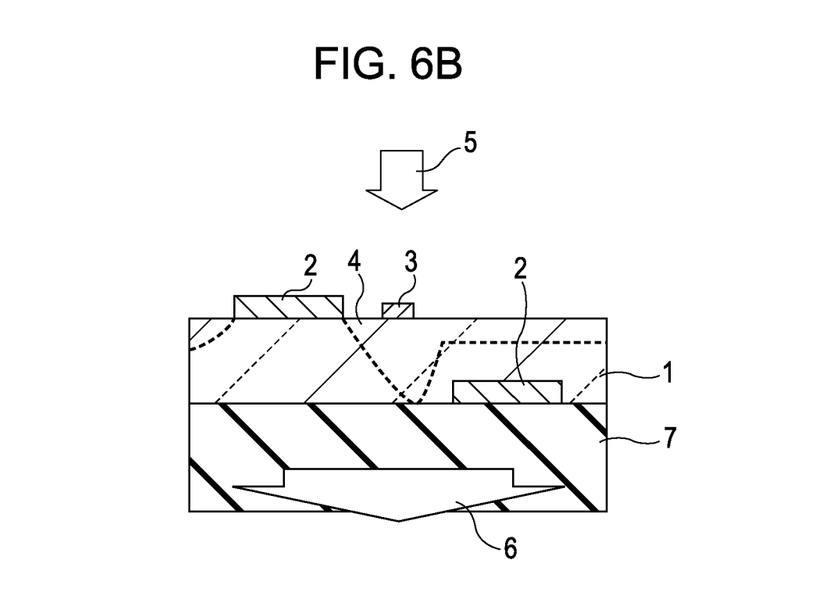
FIG. 6B is a sectional view taken along the line VIB-VIB of FIG. 6A.
Figure 7A:
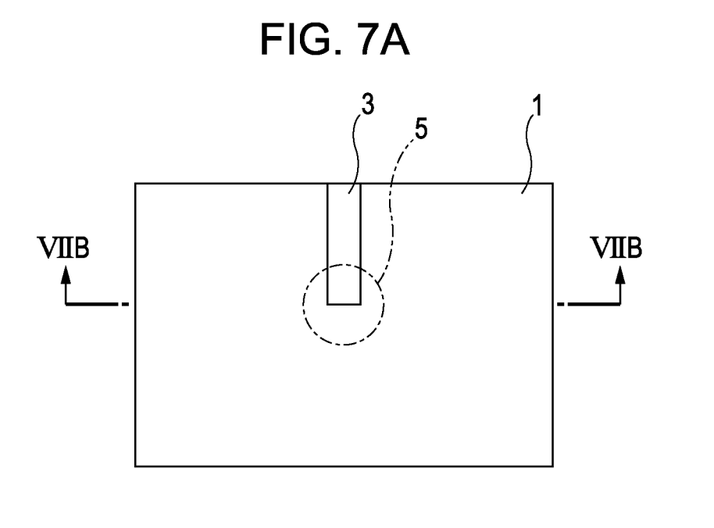
FIG. 7A is a top view of still another modification example of the photoconductive device of the first embodiment.
Figure 7B:
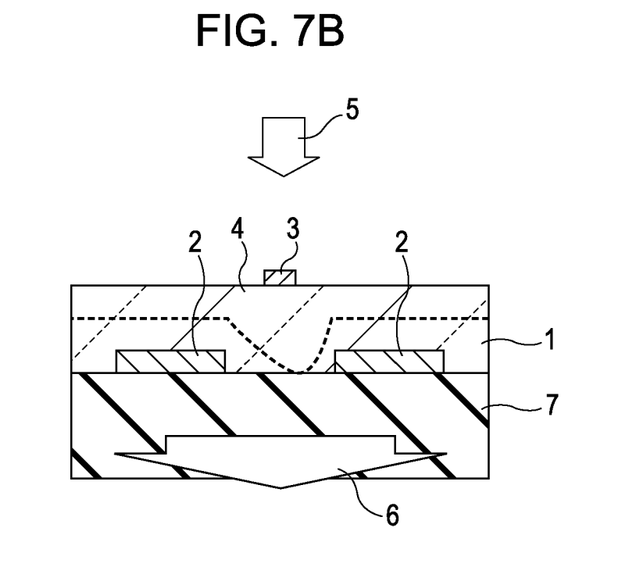
FIG. 7B is a sectional view taken along the line VIIB-VIIB of FIG. 7A.

As described above, the pair of electrodes 2 arranged in such a manner as to be in contact with the photoconductive layer 1 may be in direct contact with the photoconductive layer 1, or may be in indirect contact with the photoconductive layer 1 with, for example, an insulator layer or a contact layer therebetween. The pair of electrodes 2 are provided so as to apply an electric field to the photoconductive layer 1 in the gap between the pair of electrodes 2. The pair of electrodes 2 may desirably be constituted by a conductive material to lower the resistance thereof. Examples of the materials used for the pair of electrodes 2 include gold germanium (AuGe)/nickel (Ni)/gold (Au) and titanium (Ti)/gold (Au). The pair of electrodes 2 have pads for externally applying voltages (see FIG. 1C). Regarding the pair of electrodes 2, one of the pair of electrodes 2 may be on the substrate 7 side of the photoconductive layer 1 as illustrated in FIGS. 6A and 6B. In addition, both of the pair of electrodes 2 may be on the substrate 7 side of the photoconductive layer 1 as illustrated in FIGS. 7A and 7B.

Figure 1D:
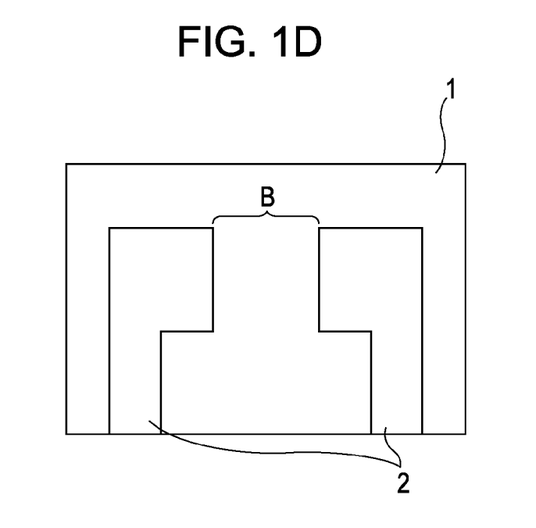
FIG. 1D is a top view of an area B of the photoconductive device of the first embodiment.

The third electrode arranged in such a manner as to be in contact with the photoconductive layer may also be in direct contact with the photoconductive layer 1 or may be in indirect contact with the photoconductive layer 1 with, for example, an insulator layer or a contact layer therebetween. The third electrode 3 is arranged in such a manner as not to be in contact with the pair of electrodes 2 to control a voltage to be applied independently of a voltage applied to the pair of electrodes 2. The third electrode 3 is provided to adjust the thickness and the like of the depletion layer 4 in the photoconductive layer 1 near the third electrode 3. An example of a material used for the third electrode 3 is Ti/Au. The third electrode 3 also has a pad for externally applying a voltage (see FIG. 1C). At least part of the third electrode 3 is arranged in such a position as to increase the resistance of the photoconductive device. Hence, at least part of the third electrode 3 is arranged in a position allowing adjustment of the thickness and the like of the depletion layer 4 of the photoconductive layer 1 in the gap between the pair of electrodes 2. In other words, the third electrode 3 is formed in a position in contact with a portion of the photoconductive layer 1 within a range over which an electric field caused by a voltage applied across the pair of electrodes 2 extends (see FIGS. 1A and 1B). More preferably, at least part of the third electrode 3 is in contact with an area of the photoconductive layer 1 where the electric field strength is equal to or more than 1/e of the average electric field strength of the portion of the photoconductive layer 1 within a region where photo-excited carriers are generated. This configuration allows the thickness of the depletion layer 4 to be controlled by the third electrode 3 using a low (close to zero) voltage. Further, it is desirable that at least part of the third electrode 3 be included or in contact with an area of the photoconductive layer 1 which includes the shortest path in the gap between the pair of electrodes 2. This is because increasing the resistance of the shortest path between the electrodes in the gap between the pair of electrodes 2 is effective for increasing the resistance of the whole photoconductive device. For instance, in the photoconductive device illustrated in FIGS. 1A to 1C, at least part of the third electrode 3 is preferably in contact with an area (area B in FIG. 1D) where the distance between the pair of electrodes 2 is the shortest.

The principle of generating the terahertz wave 6 will now be described. The photoconductive layer 1, when irradiated with the excitation light 5, absorbs the excitation light 5 and generates photo-excited carriers. The photoconductive layer 1 that is within the gap between the pair of electrodes 2 is irradiated with the excitation light 5 (see FIG. 1B). The generated photo-excited carriers are accelerated by an electric field applied by the pair of electrodes 2 to the gap between the pair of electrodes 2, whereby a current flowing through the photoconductive layer 1 changes with respect to time. In accordance with the current changing with respect to time, the terahertz wave 6 is radiated. The electric field strength of the terahertz wave 6 is given by the following equation in a simplified way in the case of a far field.

$$E_{THz} \propto dJ/dt$$

$E_{THz}$: the electric field strength of the terahertz wave 6, J: current, and t: time.

This equation shows that the electric field strength of the terahertz wave 6 increases as the change in current with respect to time in the photoconductive layer 1 increases. The change in current with respect to time is expressed by the following equation.

$$dJ/dt = (d(nv)/dt) = e((dn/dt)v + n(dv/dt))$$

e: quantum of electricity, n: carrier density, and v: carrier velocity.

Hence, it can be said that the electric field strength of the terahertz wave 6 increases as the amount of generated photo-excited carriers and the acceleration of the carriers increase. When pulse light is used as the excitation light 5, the photoconductive layer 1 generates photo-excited carriers based on the excitation light 5, and momentarily conducts. As is generally known, the characteristics of the terahertz wave 6, such as radiation intensity, a pulse width, and a frequency depend on the pulse width of the excitation light 5, the amount of carriers generated by the photoconductive layer 1, carrier mobility, electric field distribution within the photoconductive layer 1, and the like. The pair of electrodes 2 often is shaped like an antenna in the vicinity of the irradiation area with the excitation light 5 to radiate the terahertz wave 6 outwards. The shape of the antenna is, for example, a dipole antenna or a bow tie antenna.

The incident direction of the excitation light 5 may be any of the substrate 7 side, the side opposite the substrate side 7, and the end surface side of the photoconductive layer 1. The excitation light 5 is not blocked by the third electrode 3 if the excitation light 5 is input to the photoconductive layer 1 from a side without the third electrode 3. For instance, in the case of FIG. 1B, the excitation light 5 is not blocked by the third electrode 3 if the excitation light 5 is input from the substrate 7 side. In the case where the excitation light 5 is thus input from the substrate 7 side, the substrate 7 preferably is made of a material which absorbs only a small amount of the excitation light 5. In addition, the irradiation area with the excitation light 5 preferably includes the gap between the pair of electrodes 2, as described above. The reason for this is that generation of photo-excited carriers in a position with high electric field strength will increase the acceleration of the photo-excited carriers, thereby increasing the radiation intensity of the terahertz wave 6. Further, since the area where the distance between the pair of electrodes 2 is the smallest generally is an area where the strength of an electric field is the highest, such an area is preferably irradiated with the excitation light 5.

Next, factors for increasing the radiation intensity of the terahertz wave 6 are described. The radiation intensity of the terahertz wave 6 is effectively increased when the lifetime of carriers in the photoconductive layer 1 is short, the mobility is high, sufficient amount of the excitation light 5 is absorbed by the photoconductive layer 1, and the density of carriers in the photoconductive layer 1 is low. If the lifetime of carriers is short, photo-excited carriers generated by a pulse at a given time disappear before the subsequent pulse arrives. Hence, an electric field applied to photo-excited carriers generated by the subsequent pulse is prevented from being blocked by the carriers generated by the pulse one cycle ahead. When the electric field is blocked, the radiation intensity of the terahertz wave 6 is decreased since the acceleration of carriers is decreased. However, this can be avoided when the lifetime of carriers is short. High mobility allows the acceleration of the carriers to be increased, thereby increasing the radiation intensity of the terahertz wave 6. When a sufficient amount of the excitation light 5 is absorbed by the photoconductive layer 1, many photo-excited carriers are generated, whereby the radiation intensity of the terahertz wave 6 can be increased. If the density of carriers in the photoconductive layer 1 is low, a dark current flowing through a photoconductive device can be decreased. Hence, a current flowing through the photoconductive device can be decreased even when a high voltage is applied, whereby generation of damage to the photoconductive device due to a large current is suppressed. In addition, since carriers that exist while irradiation with the excitation light 5 is not performed decrease in number, the possibility of blocking an electric field applied to photo-excited carriers can be lowered. These can increase the radiation intensity of the terahertz wave 6. Further, even when the voltage externally applied across the pair of electrodes 2 is lowered, a decrease in the electric field applied to the photoconductive layer 1 is less than that in the case where the carrier density of the photoconductive layer 1 is high. Hence, a voltage that an external voltage source has to apply can be lowered, whereby the cost of the external voltage source is lowered.

The effect of providing the third electrode 3 is described. As described above, shortening of the lifetime of carriers is an effective method of increasing the radiation intensity of the terahertz wave 6. To shorten the lifetime of carriers, a photoconductive layer generally is often grown up at low temperatures. However, this process increases the density of carriers, leading to a decrease in an acceleration electric field applied to photo-excited carriers, and hence a decrease in the radiation intensity of the terahertz wave 6. One solution may be to perform annealing subsequent to the growth of a photoconductive layer to lower the carrier density. However, annealing generally lowers the mobility of the photoconductive layer. In this manner, means for lowering the carrier density may worsen the factors necessary for increasing the radiation intensity of the terahertz wave 6. Hence, the photoconductive device according to the present embodiment is provided with the third electrode 3 as means for decreasing the carrier density in the photoconductive layer 1. As a result of this structure, the photoconductive layer 1 which has been prepared either by using or without using a low-temperature growth method can be used, as described above.

The third electrode 3 arranged on the upper surface of the photoconductive layer 1 as illustrated in FIG. 1A forms a Schottky contact between the photoconductive layer 1 and itself. On the upper surface of the photoconductive layer 1, the depletion layer 4 is formed due to defects on the surface of the photoconductive layer 1. The depletion layer 4 has a small density of carriers and a high resistance. When the thickness of the depletion layer 4 having such properties is smaller than that of the photoconductive layer 1, a conductive area having a low resistance is provided between the pair of electrodes 2. This unfavorably decreases the resistance of the photoconductive device. Hence, it is preferable to increase the thickness of the depletion layer 4.

Since a photoconductive device is damaged by a large current, it is preferable to suppress a current by suppressing a voltage applied across the pair of electrodes 2 when there exists a conductive layer having a low resistance. On the other hand, it is effective to increase the voltage applied across the pair of electrodes 2 to increase the radiation intensity of the terahertz wave 6. Hence, when the low-resistance conductive layer remains in the photoconductive layer 1, the radiation intensity of the terahertz wave 6 is suppressed. Here, the thickness of the depletion layer 4 can be changed by applying a voltage to the third electrode 3. When the carriers are electrons, the thickness of the depletion layer 4 is increased by applying a minus voltage to the third electrode 3. In this manner, the low-resistance conductive area between the pair of electrodes 2 can be removed by making the thickness of the depletion layer 4 reach the thickness of the photoconductive layer 1 (preferably, with a sufficient area of the depletion layer 4). Accordingly, by increasing the resistance of the photoconductive device, a high electric field can be applied, whereby the radiation intensity of the terahertz wave 6 is increased.

Figure 3A:
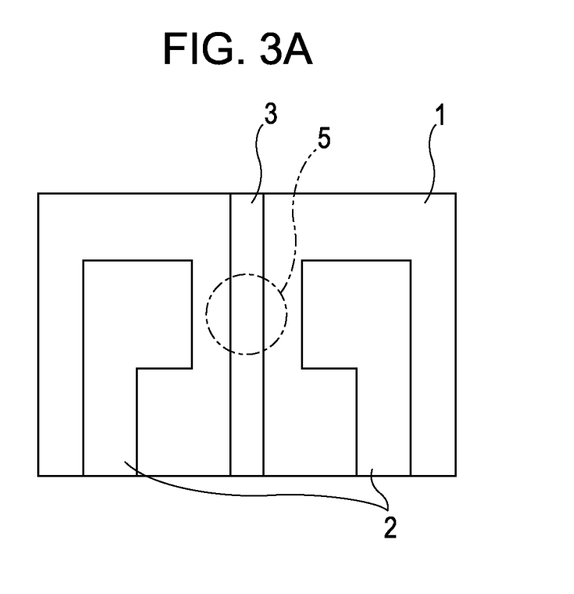
FIG. 3A is a top view of a modification example of the photoconductive device of the first embodiment.
Figure 3B:
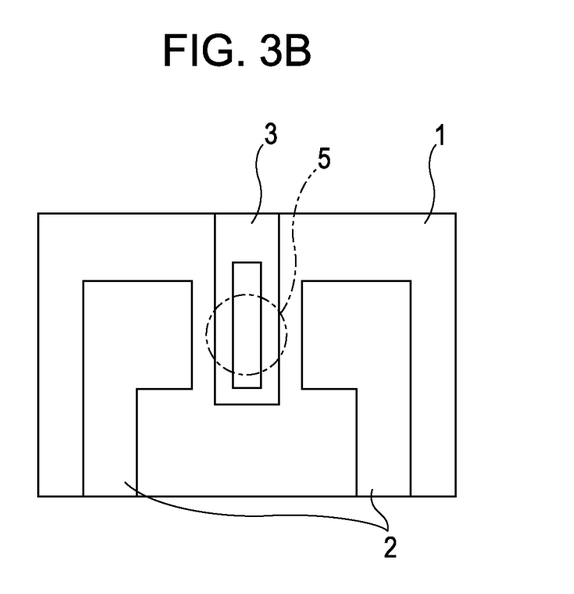
FIG. 3B is a top view of another modification example of the photoconductive device of the first embodiment.

Any arrangement, shape, and the like of the third electrode 3 may be used as long as the thickness of the depletion layer 4 formed in the photoconductive layer 1 between the pair of electrodes 2 can be increased. For example, the third electrode 3 may be arranged as illustrated in FIG. 3A. In this case, the third electrode 3 extends further into the gap between the pair of electrodes 2 than in FIG. 1A. This makes it possible to reduce the size of the low-resistance conductive region (region where a depletion layer is not formed) that exists in the photoconductive layer 1 between the pair of electrodes 2. As a result, the resistance is increased more than in the photoconductive device illustrated in FIG. 1A. Also in the photoconductive device illustrated in FIG. 3A, the excitation light 5 may be input to the photoconductive layer 1 from the substrate 7 side, thereby preventing the excitation light 5 from being blocked by the third electrode 3. Referring to FIG. 3B, the third electrode 3 may have a hole, in a portion thereof which is irradiated with the excitation light 5, to allow the excitation light 5 to pass therethrough. In this case, the amount of the excitation light 5 input can be increased.

Hereinafter, more detailed exemplary structures and operations of the photoconductive devices are described. The substrate 7 is made of SI-InP, the photoconductive layer 1 is made of InGaAs (In:Ga ratio=0.53:0.47) with lattice matching with the SI-Inp of the substrate 7, the pair of electrodes 2 are made of AuGe/Ni/Au, and the third electrode 3 is made of Ti/Au.

The photoconductive layer 1 is formed on the substrate 7 using a molecular beam epitaxial (MBE) growth method. The pair of electrodes 2 and the third electrode 3 can be formed using a lift-off process. AuGe/Ni/Au forms ohmic contact with the photoconductive layer 1 through an alloy process (alloy temperature is 400° C., for example). Schottky contact may be used for the contact state of the pair of electrodes 2, as in the case of Ti/Au. In this case, since an alloy process is not required, irregularities in the shape of the surface or interface are reduced.

Pulse light having a wavelength of the 1.5 μm band generated by an erbium (Er) fiber laser light source is used as the excitation light 5. The pulse width of this pulse light is typically 100 fs. The repetition frequency of the pulses may be 50 MHz. The pair of electrodes 2 can apply an electric field to the photoconductive layer 1. The pair of electrodes 2, which have a gap therebetween as illustrated in FIG. 1A, can apply an electric field to the photoconductive layer 1, by applying different voltages to the left and right sides of the gap. The gap has a size of 5 μm. The antenna portion of the pair of electrodes 2 has the shape of a dipole antenna, and has a total length of 25 μm in the horizontal direction of the substrate 7, in the section along the line IB-IB.

Here, the plasma frequency in the photoconductive layer 1 is made smaller than the frequency range of the terahertz wave 6 over the whole antenna to reduce the loss of the terahertz wave 6 in the photoconductive layer 1. As is generally known, the plasma frequency can be lowered by lowering the carrier density, for example. In the photoconductive layer 1, the terahertz wave 6 extends in the order of the length of the antenna and is radiated outward from the antenna. Hence, the plasma frequency is appropriately made to satisfy the condition described above. In the present example, the plasma frequency is about 100 GHz when the carrier density of the photoconductive layer 1 is $1\times10^{13}$ cm$^{-3}$, and exceeds about 10 THz when the carrier density of the photoconductive layer 1 is $1\times10^{17}$ cm$^{-3}$.

Figure 2A:
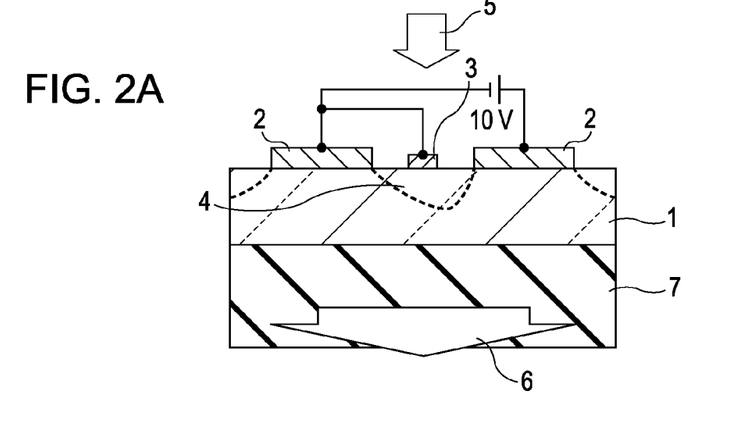
FIG. 2A is a sectional view of the photoconductive device of the first embodiment for explaining changes in the thickness and area of the depletion layer.
Figure 2B:
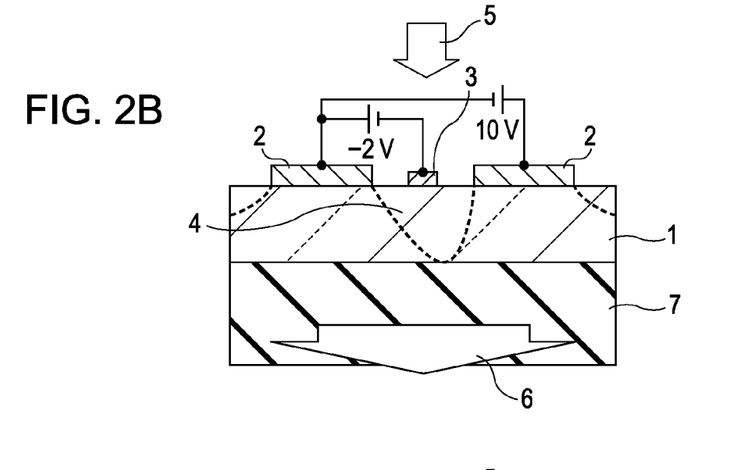
FIG. 2B is a sectional view of the photoconductive device of the first embodiment for explaining changes in the thickness and area of a depletion layer.
Figure 2C:
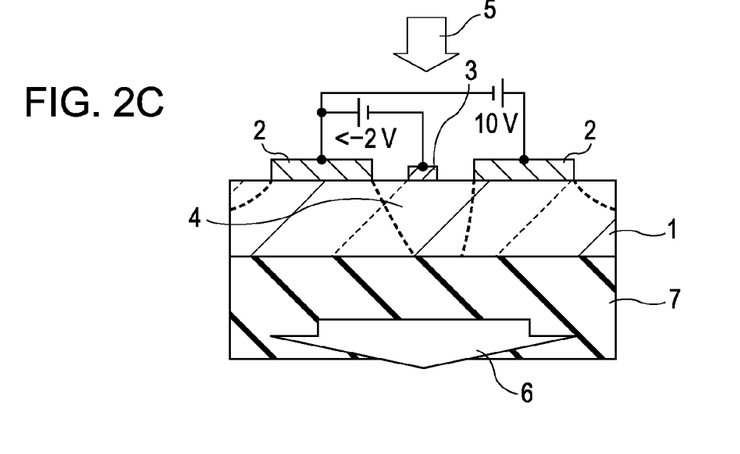
FIG. 2C is a sectional view of the photoconductive device of the first embodiment for explaining changes in the thickness and area of the depletion layer.

The thickness of the photoconductive layer 1 is made to be 1.6 μm. In other words, the photoconductive layer 1 is made to have a thickness sufficient for absorbing the excitation light 5 to generate many photo-excited carriers and thereby increase the radiation intensity of the terahertz wave 6. For instance, in the case where the photoconductive layer 1 is made of InGaAs having an optical absorption length of 1 μm at the wavelength of the excitation light 5, the photoconductive layer 1 having a thickness of 1.6 μm can absorb about 80% of the excitation light 5. Here, the thickness of the depletion layer 4 of the photoconductive layer 1 made of InGaAs is, for example, 0.8 μm, which is smaller than the thickness (1.6 μm) of the photoconductive layer 1, and hence, a low-resistance conductive region remains as illustrated in FIG. 2A. In FIGS. 2A to 2C, a reference voltage of 0 V is applied to one (left side electrode in FIGS. 2A to 2C) of the pair of electrodes 2. The other (right side electrode in FIGS. 2A to 2C) of the pair of electrodes 2 has an applied voltage of 10 V. Reflecting the state of the applied voltages, the depletion layer 4 does not have a left-right symmetric shape as illustrated in FIGS. 2A to 2C. Here, assume that −2 V is applied to the third electrode 3 (see FIG. 2B). Then the depletion layer 4 becomes thicker and extends to the lower surface of the photoconductive layer 1. In other words, the low-resistance conductive layer disappears from the gap between the pair of electrodes 2. Hence, a high voltage difference can be applied to the photoconductive layer 1, whereby the radiation intensity of the terahertz wave 6 is increased.

Referring to FIG. 2B, a portion of the depletion layer 4 that reaches the lower surface of the photoconductive layer 1 first in accordance with application of a minus voltage to the third electrode 3 is closer to one of the pair of electrodes 2 having a plus voltage applied thereto. When the voltage applied to the third electrode 3 is increased in the minus direction, the depletion layer 4 reaches the lower surface of the photoconductive layer 1 also near the 0 V electrode side (see FIG. 2C). Here, if the voltage applied to the third electrode 3 is increased too much in the minus direction, the voltage across the third electrode 3 and the pair of electrodes 2 becomes high. This would cause damage to the device or generation of a flow of carriers in a direction opposite to the direction of the flow of carriers generated by the pair of electrodes 2. Hence, the voltage applied to the third electrode 3 is made not to exceed (in the minus direction assuming that the carriers are electrons) the voltage applied across the pair of electrodes 2. More preferably, the voltage applied to the third electrode 3 is below the voltage across the pair of electrodes 2. In other words, the absolute value of the voltage applied to the third electrode 3 is made less than the absolute value of the voltage across the pair of electrodes 2, including the case where the carriers are electron holes. In this manner, the thickness of the depletion layer 4 in the photoconductive layer 1 is controlled by applying different voltages to the third electrode 3 (depletion-layer control electrode) and the pair of electrodes 2. Here, typically, different voltages are applied to the third electrode 3 and the pair of electrodes 2 such that the reference voltage applied to one of the pair of electrodes 2 is sandwiched between the voltage applied to the other of the pair of electrodes 2 and the voltage applied to the third electrode 3.

As described above, according to the device structure of the present embodiment, the resistance of the photoconductive layer 1 can be increased. Hence, a high voltage difference can be applied to the photoconductive layer 1, whereby the radiation intensity of the terahertz wave 6 can be increased.

Second Embodiment

Figure 4A:
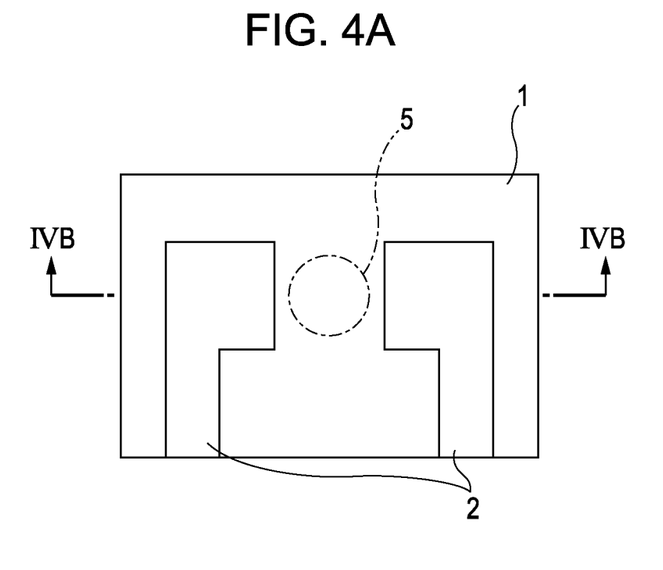
FIG. 4A is a top view of an exemplary configuration of a photoconductive device of a second embodiment.
Figure 4B:
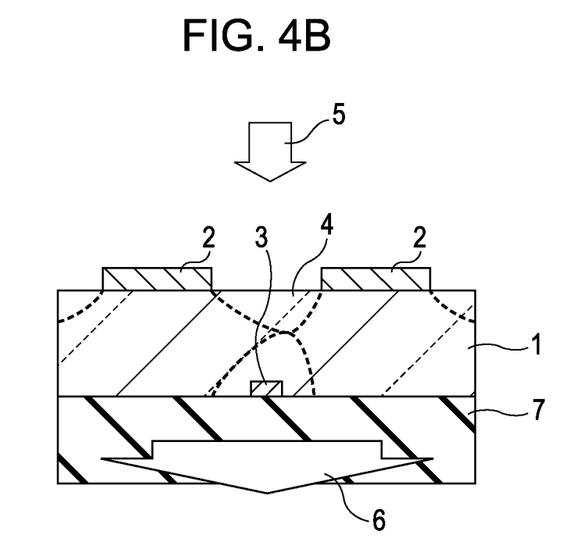
FIG. 4B is a sectional view taken along the line IVB-IVB of FIG. 4A.

A second embodiment according to the photoconductive device of the present invention relates to a modification example of the above described photoconductive device. Descriptions of the common portions described above are omitted. FIG. 4A is a top view of a photoconductive device of the present embodiment and FIG. 4B is a sectional view taken along the line IVB-IVB of FIG. 4A. Referring to FIG. 4B, the difference from the photoconductive device of the first embodiment is that a third electrode 3 is arranged between a photoconductive layer 1 and a substrate 7. To manufacture the photoconductive device according to the present embodiment, it is necessary to arrange the third electrode 3 between the photoconductive layer 1 and the substrate 7. A transcription process can be used for this purpose. Here, for example, a buffer layer, an etch stop layer, and the photoconductive layer 1 are formed on a substrate made of an appropriate material, using a molecule beam epitaxial growth method. Then, the third electrode 3 is formed by a lift-off process using a photoresist formed by photolithography. The wafer having the photoconductive layer 1 and the third electrode 3 formed thereon is, after being cut to an appropriate size, bonded to the substrate 7 including the third electrode 3 through alignment of the contact therebetween, using an appropriate method. Then, the substrate made of an appropriate material is removed by etching, and the pair of electrodes 2 are formed after the etch stop layer has been removed.

In the photoconductive device of the present embodiment, since the third electrode 3 is arranged between the photoconductive layer 1 and the substrate 7, excitation light 5 input from the upper surface of the photoconductive layer 1 is not blocked by the third electrode 3. Hence, the amount of photo-excited carries is increased, whereby the radiation intensity of a terahertz wave 6 can be increased. In addition, the third electrode 3 can adjust the thickness of a depletion layer 4 that extends from the lower surface (the substrate 7 side) of the photoconductive layer 1 into the inside of the photoconductive layer 1. Generally, another depletion layer 4 is formed on the upper surface (the side facing air) of the photoconductive layer 1. That is, since the surface is a portion where the continuity of a crystal is interrupted, many defects that trap electrons are generated, whereby electrons near the surface are trapped by the surface defects. Hence, the vicinity of the surface enters a state in which electrons are absent, i.e., a depletion layer. Accordingly, when the depletion layers 4 that extend from the upper and lower surfaces join in this case, a continuous high-resistance portion is formed in the portion of the photoconductive layer 1 between the pair of electrodes 2. For instance, when the thickness of the depletion layer 4 extending from the upper surface of the photoconductive layer 1 is 0.8 µm, a low-resistance conductive area can be removed by applying −1.5 V to the third electrode 3 for the photoconductive layer 1 having a thickness of 2 µm.

Figure 5A:
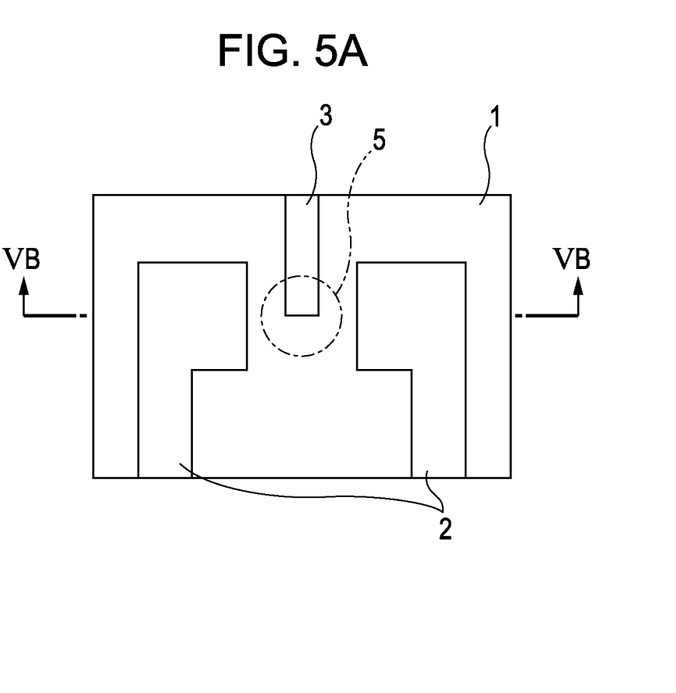
FIG. 5A is a top view of a modification example of the photoconductive device of the second embodiment.
Figure 5B:
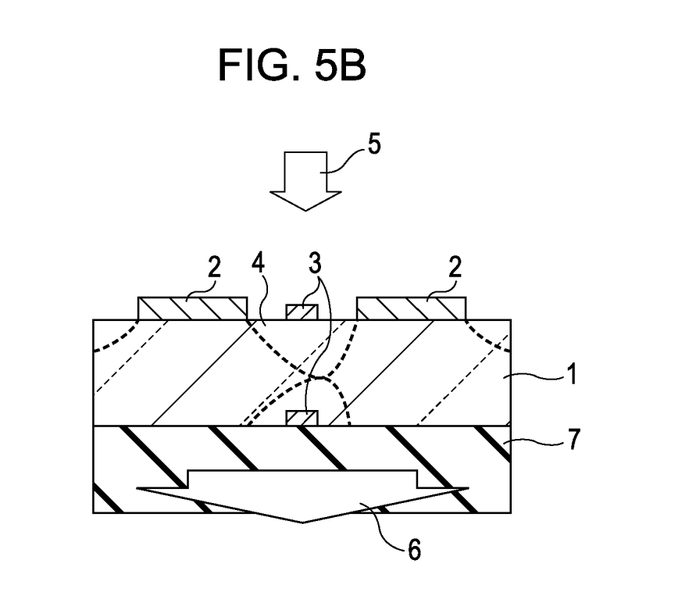
FIG. 5B is a sectional view taken along the line VB-VB of FIG. 5A.

In FIGS. 4A and 4B, the third electrode 3 is arranged between the photoconductive layer 1 and the substrate 7; however, a configuration may be used in which the photoconductive layer 1 is sandwiched between third electrodes 3 provided on the upper and lower sides, as illustrated in FIGS. 5A and 5B. The third electrodes 3 provided on the upper and lower sides of the photoconductive layer 1 may have the same voltage applied thereto or may respectively have different voltages applied thereto. Thus, the photoconductive device of the present embodiment provides an advantage in which the amount of the excitation light 5 input can be increased and/or sufficient thicknesses of the depletion layers 4 can be realized even if the absolute values of the voltages applied to the third electrodes 3 are made small.

Third Embodiment

Figure 8A:
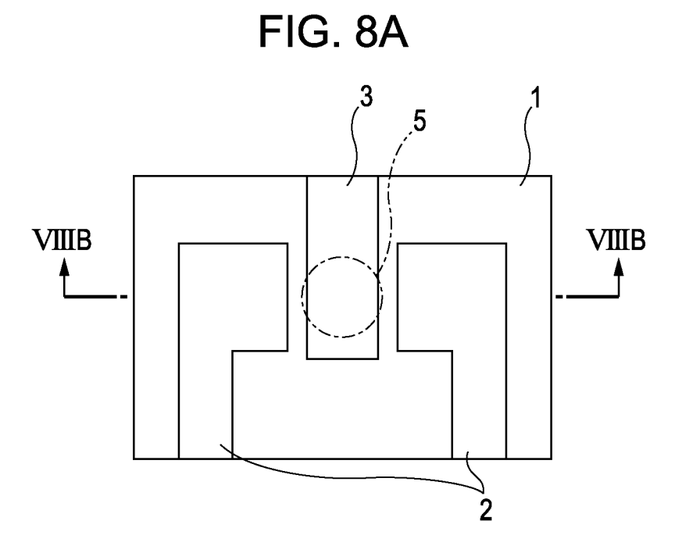
FIG. 8A is a top view of an exemplary configuration of a photoconductive device of a third embodiment.
Figure 8B:
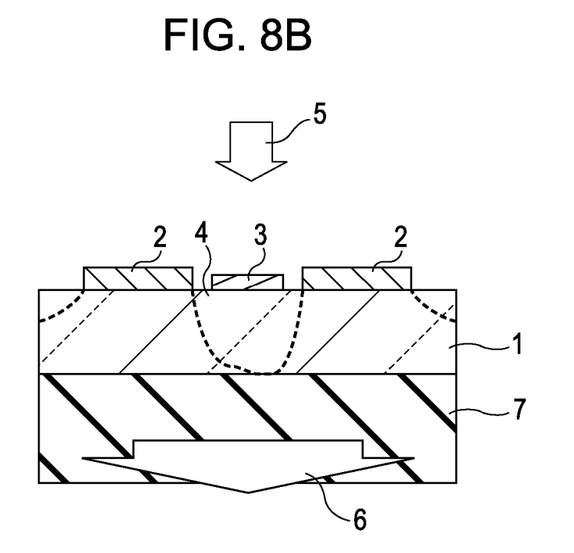
FIG. 8B is a sectional view taken along the line VIIIB-VIIIB of FIG. 8A.

A third embodiment according to the photoconductive device of the present invention relates to a modification example of the photoconductive devices described above. Descriptions of the common portions described above are omitted. FIG. 8A is a top view of a photoconductive device of the present embodiment and FIG. 8B is a sectional view taken along the line VIIIB-VIIIB of FIG. 8A. The difference from the above-described photoconductive devices is that a third electrode 3 is transparent to the wavelength of excitation light 5. An example of a material that can be used is ITO (indium tin oxide). By using a transparent electrode as the third electrode 3, the amount of the excitation light 5 input to a photoconductive layer 1 can be increased. Further, referring to FIGS. 8A and 8B, since the third electrode 3 does not block the excitation light 5, the third electrode 3 can be made larger than in the case illustrated in FIG. 1A. This makes it easy to control a depletion layer 4 in the photoconductive layer 1 and hence to control the resistance.

In this manner, the photoconductive device of the present embodiment provides an advantage in which the amount of the excitation light 5 input can be increased, and consequently the amount of generated photo-excited carriers is increased, whereby the radiation intensity of terahertz waves is increased.

Fourth Embodiment

Figure 9A:
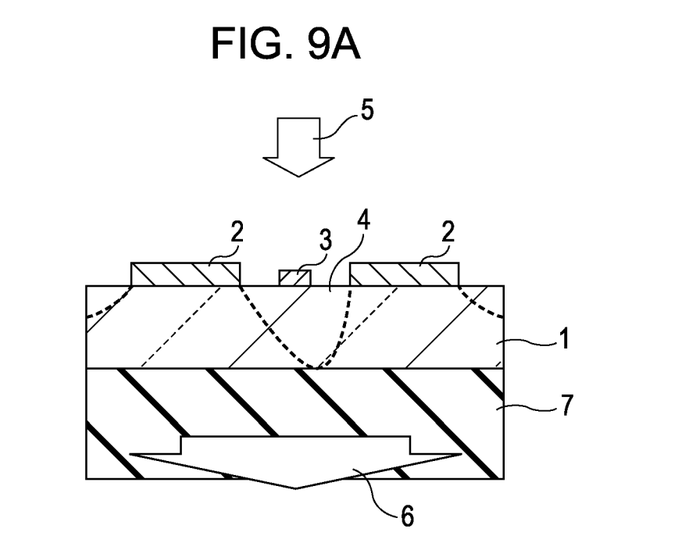
FIG. 9A is a sectional diagram illustrating an exemplary method of driving a photoconductive device of a fourth embodiment.
Figure 9B:
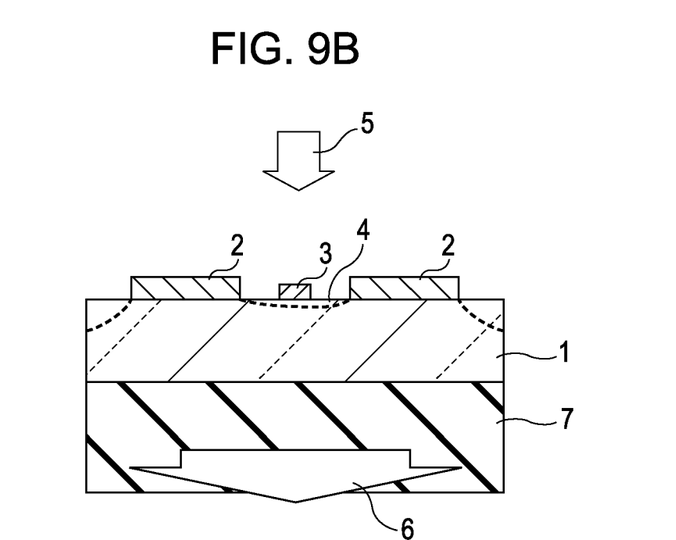
FIG. 9B is a sectional diagram illustrating an exemplary method of driving the photoconductive device of the fourth embodiment.

A fourth embodiment relates to a method of driving a photoconductive device of the present invention. Descriptions of the common portions described above are omitted. FIGS. 9A and 9B illustrate sectional views of the photoconductive device of the present embodiment corresponding to two points in time. The top view of the photoconductive device is similar to that illustrated in FIG. 1A. In the present embodiment, a voltage applied to a third electrode 3 is modulated with respect to time. For instance, in the photoconductive device illustrated in FIG. 1A, a sine wave with a center voltage of −1 V and an amplitude of 1 V is applied to the third electrode 3. Then, at the minimum voltage (−2 V), a depletion layer 4 reaches the lower surface of a photoconductive layer 1 as illustrated in FIG. 9A, and the resistance of the photoconductive layer 1 becomes maximum. On the other hand, at the maximum voltage (0 V) the width of the depletion layer 4 becomes 1 µm or less as illustrated in FIG. 9B, and the resistance of the photoconductive layer 1 becomes minimum. Here, a voltage difference of 10 V is applied to a pair of electrodes 2.

Modulation in this manner makes the radiation intensity of terahertz wave 6 maximum when the resistance of the photoconductive layer 1 is maximum, and minimum when the resistance of the photoconductive layer 1 is minimum. Hitherto, the modulation of the terahertz wave 6 has been performed by the modulation of excitation light 5 using a chopper. However, according to the present embodiment, the terahertz wave 6 can be modulated without using a chopper. The modulation frequency can be made to be 100 MHz, which is equal to the value in the case where a chopper is used. In this manner, the method of driving the photoconductive device of the present embodiment provides an advantage in which by modulating, with respect to time, voltages applied to a depletion layer control electrode and at least one electrode of a group of electrodes, the terahertz wave 6 can be modulated without using a chopper.

Fifth Embodiment

Figure 10A:
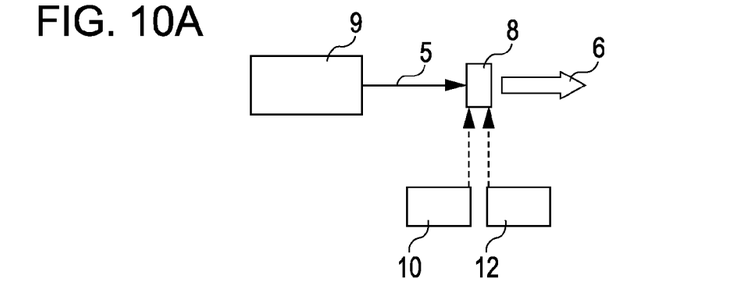
FIG. 10A is a diagram illustrating an exemplary configuration of a terahertz wave generation apparatus of a fifth embodiment.

A fifth embodiment relates to a terahertz wave generation apparatus using the photoconductive device according to the present invention. Also here, descriptions of the common portions described above are omitted. Referring to FIG. 10A which illustrates a configuration of a terahertz wave generation apparatus of the present embodiment, excitation light 5 generated by an excitation light generation unit 9 is input to a photoconductive device 8, and a gap between a pair of electrodes 2 is irradiated with the excitation light 5. A voltage from an electrode pair power source 10 is applied across the pair of electrodes 2 of the photoconductive device 8 through pads such as the ones illustrated in FIG. 1C. As described above, this configuration allows a terahertz wave 6 to be radiated from the photoconductive device 8. Similarly to the first to fourth embodiments described above, a voltage is applied to a third electrode 3 by a third-electrode power source 12.

By using the terahertz wave generation apparatus of the present embodiment described above, terahertz waves can be generated by irradiating the gap among a group of electrodes with excitation light in a state where a voltage is applied to the depletion layer control electrode and there is a voltage difference between the depletion layer control electrode and the group of electrodes. Since the photoconductive device 8 of the present invention is used, the terahertz wave 6 having high radiation intensity can be generated.

Sixth Embodiment

Figure 10B:
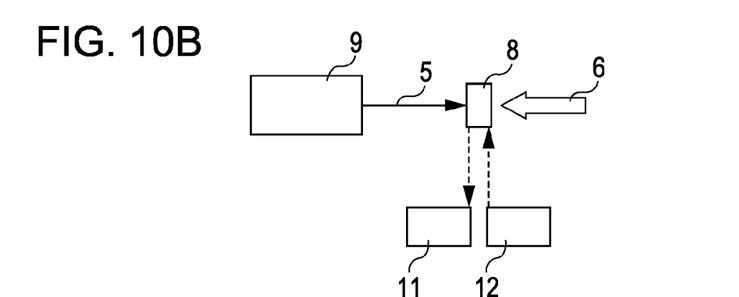
FIG. 10B is a diagram illustrating an exemplary configuration of a terahertz wave detection apparatus of a sixth embodiment.
Figure 10C:
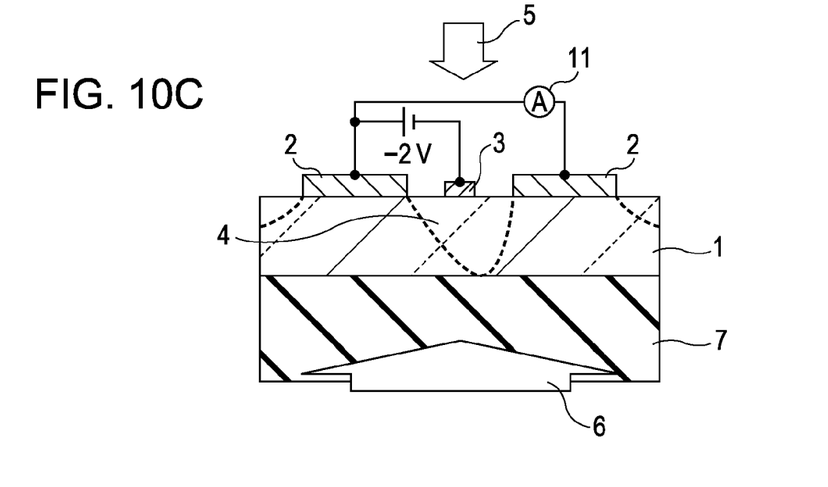
FIG. 10C is a diagram illustrating a method of driving the photoconductive device of the terahertz wave detection apparatus of the sixth embodiment.

A sixth embodiment relates to a terahertz wave detection apparatus using the photoconductive device of the present invention. Also here, descriptions of the common portions described above are omitted. FIG. 10B illustrates a configuration of a terahertz detection unit of the present embodiment, and FIG. 10C illustrates an exemplary arrangement of a current meter 11 and illustrates biasing when the photoconductive device of the present invention is used as a detection device. In the present embodiment, excitation light 5 generated by an excitation light generation unit 9 is input to a photoconductive device 8. The gap between a pair of electrodes 2 is irradiated with excitation light 5 as illustrated in FIG. 10C. The pair of electrodes 2 of the photoconductive device 8 are connected to the current meter 11 via pads such as the ones illustrated in FIG. 1C. A terahertz wave 6, which is a detection target, is also input to the pair of electrodes 2 of the photoconductive device 8. As generally known, photoexcited carriers generated by the excitation light 5 are accelerated by the electric field of the terahertz wave 6. Consequently, a current in accordance with the strength of the electric field of the terahertz wave 6 flows through the pair of electrodes 2. The terahertz wave 6 can be detected by measuring this current using the current meter 11 connected to the pair of electrodes 2. Since the pulse width of the excitation light 5 is sufficiently smaller than the pulse width of the terahertz wave 6, the value of the current shows the instantaneous electric field strength of the terahertz wave 6 during irradiation with the excitation light 5. A lock-in amplifier or the like may be used to improve the accuracy of the current detection.

Here, for example, when a voltage of −2 V, with the voltage of the pair of electrodes 2 as a voltage reference, is applied to the third electrode 3 by the third-electrode power source 12, the thickness of the depletion layer of the photoconductive layer 1 reaches the thickness of the photoconductive layer 1. This results in an increase in the resistance of the photoconductive layer 1, whereby a background current value measured by the current meter 11 is reduced. In other words, the value of the current caused by carriers other than the photoexcited carriers is decreased. Since this value is noise of the measurement, the detection accuracy of the terahertz wave 6 is increased by applying a voltage to the third electrode 3. According to the terahertz wave detection apparatus described above, a terahertz wave can be detected by measuring a current flowing through the electrodes of a group of electrodes through irradiation of the gap among the group of electrodes with excitation light and the terahertz wave in a state where a voltage is applied to a depletion layer control electrode and there is a voltage difference between the group of electrodes and the depletion layer control electrode. Since the photoconductive device 8 is used, the terahertz wave 6 can be measured with high accuracy.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-135630 filed Jun. 5, 2009, which is hereby incorporated by reference herein in its entirety.

What is claimed is:
1. An apparatus comprising:
a generation unit configured to generate excitation light;
a power source, and
a photoconductive device comprising:
a photoconductive layer configured to generate carriers upon irradiation with excitation light;
a first electrode arranged on the photoconductive layer;

a second electrode arranged on the photoconductive layer with a gap between the first and second electrodes; and a third electrode arranged in a region over which an electric field caused by voltages applied to the first and second electrodes or an electric field caused by irradiation with a terahertz wave extends, wherein a depletion layer of the photoconductive layer is controllable by a voltage applied to the third electrode, wherein a terahertz wave is generated by irradiating the gap between the first and second electrodes with the excitation light in a state where a voltage is applied to the third electrode, the voltage being different from the voltages of the first and second electrodes, and wherein a voltage is applied to the third electrode by the power source.

2. The apparatus according to claim 1, wherein the region is a region of the photoconductive layer where an electric field strength is equal to or more than 1/e of an average electric field strength of a portion of the photoconductive device within a region where the carriers are generated.

3. The apparatus according to claim 1, wherein the third electrode is transparent to a wavelength of the excitation light.

4. The apparatus according to claim 1, configured to allow a voltage value applied to at least one of the first, second, and third electrodes to be modulated with respect to time.

5. An apparatus comprising:
a generation unit configured to generate excitation light;
a power source, and
a photoconductive device comprising:
    a photoconductive layer configured to generate carriers upon irradiation with excitation light;
    a first electrode arranged on the photoconductive layer;
    a second electrode arranged on the photoconductive layer with a gap between the first and second electrodes; and
    a third electrode arranged in a region over which an electric field caused by voltages applied to the first and second electrodes or an electric field caused by irradiation with a terahertz wave extends, wherein a depletion layer of the photoconductive layer is controllable by a voltage applied to the third electrode, wherein a terahertz wave is detected by irradiating the gap between the first and second electrodes with the excitation light and the terahertz wave in a state where a voltage is applied to the third electrode, the voltage being different from the voltages of the first and second electrodes, and by measuring a current flowing between the first and second electrodes, and wherein a voltage is applied to the third electrode by the power source.

6. The apparatus according to claim 5, wherein the region is a region of the photoconductive layer where an electric field strength is equal to or more than 1/e of an average electric field strength of a portion of the photoconductive device within a region where the carriers are generated.

7. The apparatus according to claim 5, wherein the third electrode is transparent to a wavelength of the excitation light.

8. The apparatus according to claim 5, configured to allow a voltage value applied to at least one of the first, second, and third electrodes to be modulated with respect to time.

* * * * *